US012749196B2

(12) United States Patent
Zhang et al.

(10) Patent No.: US 12,749,196 B2
(45) Date of Patent: Sep. 29, 2026

(54) LEFT ATRIAL APPENDAGE SEGMENTATION AND QUANTIFICATION IN 3D AND 4D CARDIAC ULTRASOUND

(71) Applicant: Siemens Medical Solutions USA, Inc., Malvern, PA (US)

(72) Inventors: Yue Zhang, Jersey City, NJ (US); Puneet Sharma, Princeton Junction, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 312 days.

(21) Appl. No.: 18/539,651

(22) Filed: Dec. 14, 2023

(65) Prior Publication Data

US 2025/0200752 A1 Jun. 19, 2025

(51) Int. Cl.
*G06T 7/11* (2017.01)
*A61B 8/00* (2006.01)
(Continued)

(52) U.S. Cl.
CPC ................ *G06T 7/11* (2017.01); *A61B 8/085* (2013.01); *A61B 8/0883* (2013.01); *A61B 8/12* (2013.01); *A61B 8/466* (2013.01); *A61B 8/469* (2013.01); *A61B 8/48* (2013.01); *A61B 8/483* (2013.01); *A61B 8/5207* (2013.01); *G06T 7/149* (2017.01); *G06T 7/246* (2017.01); *G06T 7/62* (2017.01);
(Continued)

(58) Field of Classification Search
CPC ... G06T 7/11; G06T 7/149; G06T 7/62; G06T 2207/10136; G06T 2207/20081; G06T 2207/20132; G06T 2207/30048; G06T 7/246; G06T 7/73; G06T 2207/10028; G06T 2207/20104; G06T 7/0012; G06T 7/60; G06T 17/00; G06T 2207/10132; G06T 2207/20084; A61B 8/0883; A61B 8/12; A61B 8/466; A61B 8/469; A61B 8/483; A61B 8/5207; A61B 8/5223; A61B 8/085; A61B 8/48
See application file for complete search history.

(56) References Cited

U.S. PATENT DOCUMENTS

| | | | |
|---|---|---|---|
| 7,516,556 | B2 | 4/2009 | Yepes Segovia et al. |
| 7,783,094 | B2 | 8/2010 | Collins et al. |

(Continued)

FOREIGN PATENT DOCUMENTS

| | | | |
|---|---|---|---|
| AU | 200620164 | B2 | 1/2011 |
| JP | 2006192254 | A | 7/2006 |

(Continued)

OTHER PUBLICATIONS

Xiaofei Sun et al 2023 Phys. Med. Biol. 68 125007 Published Jun. 12, 2023 (Year: 2023).*

(Continued)

*Primary Examiner* — Matthew C Bella
*Assistant Examiner* — Shane Wrensford Codrington

(57) ABSTRACT

Systems and methods for real time three-dimensional left atrial appendage (LAA) quantification. Deep learning is used to perform LAA segmentation, tracking and live quantification on critical measurement in 4D ultrasound sequences. The collected information may be used for device selection and anomaly detection to assist early-phase disease finding.

16 Claims, 11 Drawing Sheets

(51) Int. Cl.

| | |
|---|---|
| ***A61B 8/08*** | (2006.01) |
| ***A61B 8/12*** | (2006.01) |
| ***G06T 7/00*** | (2017.01) |
| ***G06T 7/149*** | (2017.01) |
| ***G06T 7/246*** | (2017.01) |
| ***G06T 7/60*** | (2017.01) |
| ***G06T 7/62*** | (2017.01) |
| ***G06T 7/73*** | (2017.01) |
| ***G06T 17/00*** | (2006.01) |

(52) U.S. Cl.

CPC ...... *G06T 7/73* (2017.01); *G06T 2207/10028* (2013.01); *G06T 2207/10136* (2013.01); *G06T 2207/20081* (2013.01); *G06T 2207/20104* (2013.01); *G06T 2207/20132* (2013.01); *G06T 2207/30048* (2013.01)

(56) References Cited

U.S. PATENT DOCUMENTS

| | | | |
|---|---|---|---|
| 7,940,995 B2 | 5/2011 | Lee et al. | |
| 12,376,830 B2 | 8/2025 | Miyaki et al. | |
| 2012/0065499 A1 | 3/2012 | Chono | |
| 2019/0374251 A1 | 12/2019 | Lin et al. | |
| 2024/0024037 A1* | 1/2024 | Matsumura .......... | A61B 8/0883 |
| 2024/0206852 A1* | 6/2024 | Jiang ...................... | A61B 8/469 |

FOREIGN PATENT DOCUMENTS

| | | |
|---|---|---|
| JP | 2006305361 A | 11/2006 |
| JP | 2008511889 A | 4/2008 |
| JP | 2008541889 A | 11/2008 |
| JP | 2022164469 A | 10/2022 |
| WO | 2010134512 A1 | 11/2010 |

OTHER PUBLICATIONS

Guicheng Liang, Beizhu Xu, Shirong Wang, Chengxuan Li, Guoqiang Zhong. Imaging with intracardiac echocardiography compared to transesophageal echocardiography during left atrial appendage occlusion. Rev. Cardiovasc. Med. 2020, 21(1), 93-101. https://doi.org/10.31083/j.rcm.2020.01.569 (Year: 2020).*

Huang, Y., He, J., Wu, X., Zhao, X. and Wu, J. (2021), Tracking 3D ultrasound anatomical landmarks via three orthogonal plane-based scale discriminative correlation filter network. Med. Phys., 48: 2127-2135. https://doi.org/10.1002/mp.14798 (Year: 2021).*

Kinda, Anna & Saddi, Kinda & Rousson, Mikaël & Cheriet, Farida. (2007). Global-to-Local Shape Matching for Liver Segmentation in CT Imaging. Proc. MICCAI Workshop 3-D Segmentation Clinic: A Grand Challenge. (Year: 2007).*

Extended European Search Report (EESR) mailed Apr. 14, 2025 in related European Patent Application No. 24219437.1.

Moghadam Pakizeh et al:; "Semi-Automated Algorithm for Segmentation of the Left Atrial Appendage Landing Zone: Application in Left Atrial Appendage Occlusion Procedures"; Journal of Biomedical Physics and Engineering; Apr. 1, 2020 (Apr. 1, 2020); XP093266885; ISSN: 2251-7200; DOI: 10.31661/jbpe.v0i0.1912-1019.

Crestan Albereta et al:; "Automatic Segmentation Framework for Left Atrial Appendage Orifice Identification from 3D Echocardiography"; Apr. 4, 2024.

Jin, Cheng, et al. "Detection of Substances in the Left Atrial Appendage by Spatiotemporal Motion Analysis Based on 4D-CT." Statistical Atlases and Computational Models of the Heart. ACDC and MMWHS Challenges: 8th International Workshop, STACOM 2017.

Jin, Cheng, et al. "Left atrial appendage segmentation and quantitative assisted diagnosis of atrial fibrillation based on fusion of temporal-spatial information." Computers in biology and medicine 96 (2018): 52-68.

Leventic, Hrvoje, et al. "A survey of left atrial appendage segmentation and analysis in 3D and 4D medical images." The 28th International Conference on Systems, Signals and Image Processing, IWSSIP 2021. 2021.

Morais, Pedro, et al. "Fast segmentation of the left atrial appendage in 3-D transesophageal echocardiographic images." IEEE transactions on ultrasonics, ferroelectrics, and frequency control 65.12 (2018): 2332-2342.

Park, Jai-Wun, et al. "Left atrial appendage closure with Amplatzer cardiac plug in atrial fibrillation: initial European experience." Catheterization and Cardiovascular Interventions 77.5 (2011): 700-706.

Zheng, Yefeng, et al. "Four-chamber heart modeling and automatic segmentation for 3-D cardiac CT vols. using marginal space learning and steerable features." IEEE transactions on medical imaging 27.11 (2008): 1668-1681.

* cited by examiner

LEFT ATRIAL APPENDAGE SEGMENTATION AND QUANTIFICATION IN 3D AND 4D CARDIAC ULTRASOUND

FIELD

This disclosure relates to left atrial appendage segmentation and analysis.

BACKGROUND

The Left atrial appendage (LAA) is a small pouch extending off the side of the left atrium in the heart that functions as a decompression chamber when atrial pressure is high. The LAA plays a key role in the thromboembolic risk associated with atrial fibrillation and may also have a possible triggering effect of atrial tachyarrhythmia. Atrial fibrillation (A-fib) is a type of abnormal heart rhythm where the upper chambers of the heart beat irregularly and rapidly, increasing the risk of blood clots forming in the heart. If a blood clot in the left upper chamber (left atrium) breaks free from the heart area, it can travel to the brain and cause a stroke, a leading cause of death. Studies have shown that the Left atrial appendage (LAA) is a particularly common site where blood clots form in people with A-fib.

Understanding the morphology and function of LAA is pivotal for the treatment of A-fib. However, in most cases, it is impossible to clearly detect the LAA by an ordinary two-dimensional transthoracic echocardiography (2D TTE) alone, due to the small size and distant position of the TAA from the transducer, as well as other factors. Real-time three-dimensional echocardiography (RT-3D TEE) imaging may be used to preserve spatial and temporal resolution, and thereby significantly enhance the visualization of complex 3D structures, such as the LAA. 3D Intracardiac Echocardiography (ICE) may also be used to capture images of the LAA. However, none of the existing approaches focus on 4D ultrasound sequences such as 4D Intracardiac Echocardiography and in particular, live tracking and measurements of the LAA. Live tracking and measurements of LAA in 4D ultrasound sequences has its unique challenge including high anatomical variability in different cardiac phases and high volume of data for real-time processing.

SUMMARY

By way of introduction, the preferred embodiments described below include methods, systems, instructions, and computer readable media for real time segmentation and quantification of the LAA in 3D and 4D cardiac ultrasound.

In a first aspect, a method real time three-dimensional left atrial appendage quantification, the method comprising: acquiring a real time three-dimensional ultrasound sequence of patient; selecting a seed location of the left atrial appendage in a frame of the real time three-dimensional ultrasound sequence; cropping the frame to a region of interest based on the seed location; generating a three-dimensional left atrial appendage segmentation from the region of interest; extracting one or more landmarks from the three-dimensional left atrial appendage segmentation; slicing the three-dimensional left atrial appendage segmentation into a plurality of two-dimensional slices, wherein the plurality of two-dimensional slices each include a portion of a contour of the left atrial appendage; tracking the contour of the left atrial appendage in the plurality of two-dimensional slices and the one or more landmarks in the real time three-dimensional ultrasound sequence; generating a real time three-dimensional left atrial appendage segmentation from the tracked contour; and quantifying at least one metric from the tracked contour and/or the tracked one or more landmarks.

In an embodiment, selecting the seed location comprises: freezing the real time three-dimensional ultrasound sequence; and clicking, by a user, on the seed location inside the left atrial appendage in a frame of the frozen real time three-dimensional ultrasound sequence. The real time three-dimensional ultrasound sequence is unfrozen after selecting the seed location.

In an embodiment, cropping comprises: calculating an estimated shape and size of the left atrial appendage from a collected dataset of images of left atrial appendages of a plurality of patients; and centering the region of interest around the seed location based on the estimated shape and size.

The three-dimensional left atrial appendage segmentation may be generated using a machine trained network. The one or more landmarks may comprise at least one of ostium and neck landmarks that determine diameters of the ostium and neck area of the left atrial appendage. The contour and the one or more landmarks may be tracked in real time using respective neural networks trained using a cycle-consistency loss.

In an embodiment, at least one metric provides a diameter of the left atrial appendage across time. The diameter of the left atrial appendage may be used to determine and select properties of a device in a left atrial appendage closure procedure that matches characteristics of the patient's left atrial appendage.

In an embodiment, the real time three-dimensional ultrasound sequence is provided by an ultrasound system configured for Intracardiac Echocardiography.

In a second aspect, a system for real time three-dimensional left atrial appendage segmentation is provided. The system includes an ultrasound imaging system and processor. The ultrasound imaging system is configured to acquire a 4D ultrasound sequence of patient. The processor is configured to select a seed location of the left atrial appendage in a frame of the 4D ultrasound sequence, crop the frame to a region of interest based on the seed location, generate a three-dimensional left atrial appendage segmentation from the region of interest, extract one or more landmarks from the three-dimensional left atrial appendage segmentation, slice the three-dimensional left atrial appendage segmentation into a plurality of two-dimensional slices, wherein the plurality of two-dimensional slices each include a portion of a contour of the left atrial appendage, track the contour in the plurality of two-dimensional slices over time and the one or more landmarks in the 4D ultrasound sequence, and quantify at least one metric from the tracked contour and/or the tracked one or more landmarks.

In an embodiment, cropping comprises calculating an estimated shape and size of the left atrial appendage from a collected dataset of images of left atrial appendages of a plurality of patients; and centering the region of interest around the seed location based on the estimated shape and size.

The processor may be configured to generate the three-dimensional left atrial appendage segmentation using a machine trained network. The one or more landmarks comprises at least one of ostium and neck landmarks that determine diameters of the ostium and neck area of the left atrial appendage. The processor is configured to track the contour and the one or more landmarks in real time using respective neural networks trained using a cycle-consistency loss. The at least one metric provides a diameter of the left atrial appendage across time. The diameter of the left atrial appendage is used to determine and select properties of a device in a left atrial appendage closure procedure that matches characteristics of the patient's left atrial appendage.

In a third aspect a system is provided that includes an ultrasound imaging system, a display, an input device, and a processor. The ultrasound imaging system is configured to acquire a 4D ultrasound sequence of patient. The display is configured to display the 4D ultrasound sequence. The input device is configured to identify a seed location for a left atrial appendage in a frame of the 4D ultrasound sequence. The processor is configured to crop the frame to a region of interest based on the seed location, generate a three-dimensional left atrial appendage segmentation from the region of interest, slice the three-dimensional left atrial appendage segmentation into a plurality of two-dimensional slices, wherein the plurality of two-dimensional slices each include a portion of a contour of the left atrial appendage, track the contour in the plurality of two-dimensional slices in real time, and generate a real time three-dimensional left atrial appendage segmentation from the tracked contour.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Embodiments described herein provide systems and methods for left atrial appendage segmentation and quantification in 3D and 4D cardiac ultrasound procedures. Embodiments provide a system framework using deep learning to perform LAA segmentation, tracking and live quantification on critical measurement in 4D ultrasound sequences. The collected information may be used for device selection and anomaly detection to assist early-phase disease finding. The systems and method described herein may be applied to both 3D ultrasound volumes and 4D ultrasound sequences.

Figure 1:
FIG. 1 depicts an example image of a heart including the left atrial appendage.

FIG. 1 depicts an example left atrium 20 and surrounding structure of interest. The structure includes the left atrial appendage (LAA) 26, left inferior pulmonary vein (LIPV) 25, left superior pulmonary vein (LSPV) 28, right inferior pulmonary vein (RIPV) 22, and right superior pulmonary vein (RSPV) 24. The left ventricle or other heart chambers may be an anatomy of interest when performing an ultrasound procedure. While the embodiments described herein focus on the LAA in particular, the methods and systems may be applied to other organs, tissues, or structures that may benefit from real time segmentation and quantification.

While everyone has an LAA, the size and anatomy of the LAA in respective patients varies, as do the issues the LAA can cause. As is depicted in FIG. 1, the LAA is located on a side of the pulmonary arteries that bring in blood from the lungs. The position of the LAA can cause blood to pool there instead of flowing into the left ventricle of your heart. For patients with normal heart rhythm, the left atrial appendage squeezes rhythmically with the rest of the left atrium. This rhythmic contraction ensures that blood in the pouch is ejected when the left atrium empties into the left ventricle, where it is then pumped all over the body. However, AFib patients experience poor atrial contractions during an episode. These weak contractions, combined with blood pooling, may result in clot formation, which may form in the LAA. Anticoagulation therapy is typically used as the main embolism prevention treatment for patients with atrial fibrillation, however, it may have a poor long-term compliance and potential bleeding complications. Left atrial appendage closure/(LAAC) is a minimally invasive cardiac intervention to prevent blood clots from forming in LAA by closing it off with a device. This can significantly reduce the risk of stroke in people with A-fib who are at high risk of developing blood clots. It serves as an alternative solution for anticoagulation therapy and is recommended for people with A-fib who cannot take blood-thinning medications.

Understanding LAA morphology is a critical step towards successful LAA interventions. Additional information, for example CT data for the patient, may be collected before the procedure (sometimes days prior to the procedure) in order to help guide the LAA intervention. However, the patient's LAA's structure and characteristics may change during the intervening period. Real time segmentation and quantification may solve this issue. Existing solutions in ultrasound may only focus on 3D TEE, where no motion information of LAA may be obtained. Embodiments described herein provide live segmentation and quantification of LAA. Embodiments provide the structure tracking for both LAA landmarks as well as 2D slices. By aggregating the 2D slice tracking in 3D, the systems and methods also track 3D LAA structure in time. The resulting quantification and analysis may be used for device selection, validation and anomaly detection for early disease finding. Analyzing the changes of LAA measurement, one can perform anomaly detection to detect abnormal activities of LAA and use this to help the diagnostics and early disease finding.

Figure 2:
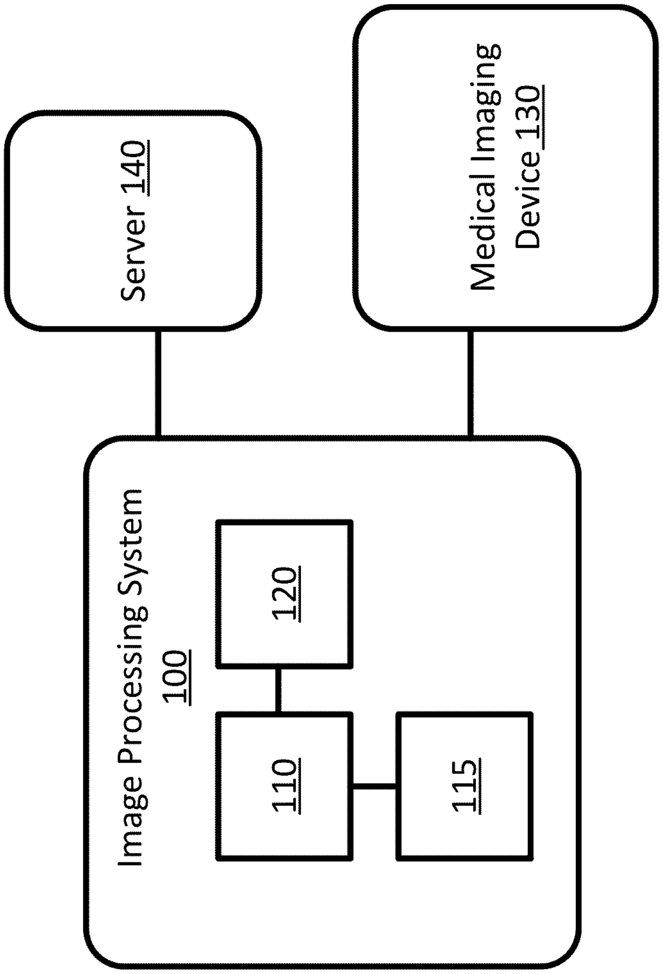
FIG. 2 depicts a system for real time quantification of a 4D ultrasound sequence according to an embodiment.

FIG. 2 depicts an ultrasound system 100 for real time quantification of a 4D ultrasound sequence. The system includes an image processing system 100, a medical imaging device 130, and optionally a server 140. The server 140 may be configured to perform any of the tasks of the image processing system 100 including processing and/or storing of the data and models. The server 140 may be or include a cloud-based platform. The image processing system 100 includes a processor 110, a memory 120, and a display 115. The image processing system 100 may be included with or coupled to the medical imaging device 130. The image processing system 100 is configured to receive the image data from the medical imaging device 130, crop and segment the LAA (or other organ) based on a seed location provided by an operator or automatically, identify landmarks in the segmented LAA, slice the segmentation into 2D slices, and track/and quantify the LAA over time using the slices and landmarks. The image processing system 100 may be further configured to generate augmented image data that depicts the contour of the LAA in real time in the 4D ultrasound sequence. The image processing system 100 may also be configured to train or store a machine learned model for these tasks. Imaging data is acquired from the medical imaging device 130 in real time for example as a 4D (3D+time) ultrasound sequence. Additional, different, or fewer components may be provided. For example, a computer network is included for remote processing of locally captured ultrasound data, for example by the server 140. As another example, a user input device (e.g., keyboard, buttons, sliders, dials, trackball, mouse, or other device) is provided for user alteration or placement of one or more markers. In yet another example, one or more devices or components used in a medical procedure such as left atrial appendage closure (LAAC) may be included. For example, devices that block the left atrial appendage's opening to keep blood clots that form in the LAA from going into the bloodstream, devices that clamp the base of the LAA to close it off, or devices that use a band or suture loop to close off the LAA among other medical devices.

The medical imaging device 130 may be an ultrasound system 130 configured to generate a live (4D) ultrasound sequence. Ultrasound imaging uses sound waves to image internal body structures. Techniques include transthoracic echocardiogram (TTE), transesophageal echocardiogram (TEE), and Intracardiac Ultrasound (ICE) among others. TTE is a non-invasive procedure where a transducer (or probe) is placed on the chest of the patient. Images are recorded using ultrasound data. For TEE, the probe is passed through a patient's esophagus in order to be near the patient's heart. The probe may have an ultrasound transducer at the tip in order to provide imaging capabilities. ICE uses a catheter transducer elements. The catheter is threaded thru a vein in the groin and up into the heart. ICE may be used to perform an echocardiogram that uses sound waves to produce detailed images of the heart's size, structure, and function, as well as detailed images of the heart's valves. The echocardiogram also can be used to measure the heart's blood volume, and the speed and direction of blood flow through the heart. In an embodiment, for a LAAC procedure, the catheter is introduced via a femoral venous access and placed either in the right atrium, the right ventricular outflow tract, coronary sinus, or the left atrium. The volumetric acquisition in real-time and in 3D allows the 4D volume ICE technology to reduce the need to acquire images from different anatomical locations wherein the coronal plane allows planar assessment of the LAA anatomy, facilitates spatial orientation, and provides circumferential peri-valvular as well as peri-device flow assessment using Color Doppler.

The processor 110 is a general processor, digital signal processor, graphics processing unit, application specific integrated circuit, field programmable gate array, artificial intelligence processor, digital circuit, analog circuit, combinations thereof, or other now known or later developed device for real time quantification of a 4D ultrasound sequence, among other processes described below. The processor 110 is a single device, a plurality of devices, or a network. For more than one device, parallel or sequential division of processing may be used. Different devices making up the processor 110 may perform different functions. In one embodiment, the processor 110 is a control processor or other processor of the medical imaging device 130. In other embodiments, the processor 110 is part of a separate workstation or computer. The processor 110 operates pursuant to stored instructions to perform various acts described herein. The processor 110 is configured by software, design, firmware, and/or hardware to perform any or all of the acts of FIGS. 3-6 and any other computations described herein.

In an embodiment, the processor 110 is configured to perform segmentation, for example using a machine trained model. The processor 110 is configured to crop and segment the live ultrasound sequence. The image segmentation extracts or identifies regions of interest (ROI) through a semiautomatic or automatic process. Segmentation divides an image into areas based on a specified description, such as segmenting body organs/tissue. The segmented data may be used for different applications such as tracking the movement of the respective organ or feature (here the LAA). The segmentation may be provided by a segmentation model and the output of the medical imaging device 130. Different types of models or networks may be trained and used for the segmentation task. The segmented data includes a plurality of voxels. Each voxel represents a three-dimensional display element. For example, a voxel represents a quantity of 3D data just as a pixel is a point or cluster of points in two-dimensional data. The processor 110 is further configured to slice the 3D segmentation of the LAA into a plurality of 2D slices and process the 2D slices in parallel. The processing of the 2D slices may include contour tracking and landmark identification across subsequent frames of the live ultrasound sequence. The processor 110 is further configured to quantify and analysis metrics for the LAA based on the tracked LAA contour and landmarks. For the segmentation, landmark detection, and tracking, the processor 110 may apply one or more trained machine learned networks or models that have been trained for the respective task (segmentation, detection, tracking, etc.).

The machine learned network(s) or model(s) may include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to the next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes.

Image data, the machine trained networks, training data, computed metrics, and other data may be stored in the memory 120. The memory 120 may be or include an external storage device, RAM, ROM, database, and/or a local memory (e.g., solid state drive or hard drive). The same or different non-transitory computer readable media may be used for the instructions and other data. The memory 120 may be implemented using a database management system (DBMS) and residing on a memory 120, such as a hard disk, RAM, or removable media. Alternatively, the memory 120 is internal to the processor 110 (e.g., cache). The instructions for implementing the processes, methods, and/or techniques discussed herein are provided on non-transitory computer-readable storage media or memories, such as a cache, buffer, RAM, removable media, hard drive, or other computer readable storage media (e.g., the memory 120). The instructions are executable by the processor 110 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor 110 or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The display 115 is configured to display or otherwise provide the model of the user to the user. The display 115 is a CRT, LCD, projector, plasma, printer, tablet, smart phone or other now known or later developed display device for displaying the output.

Figure 3:
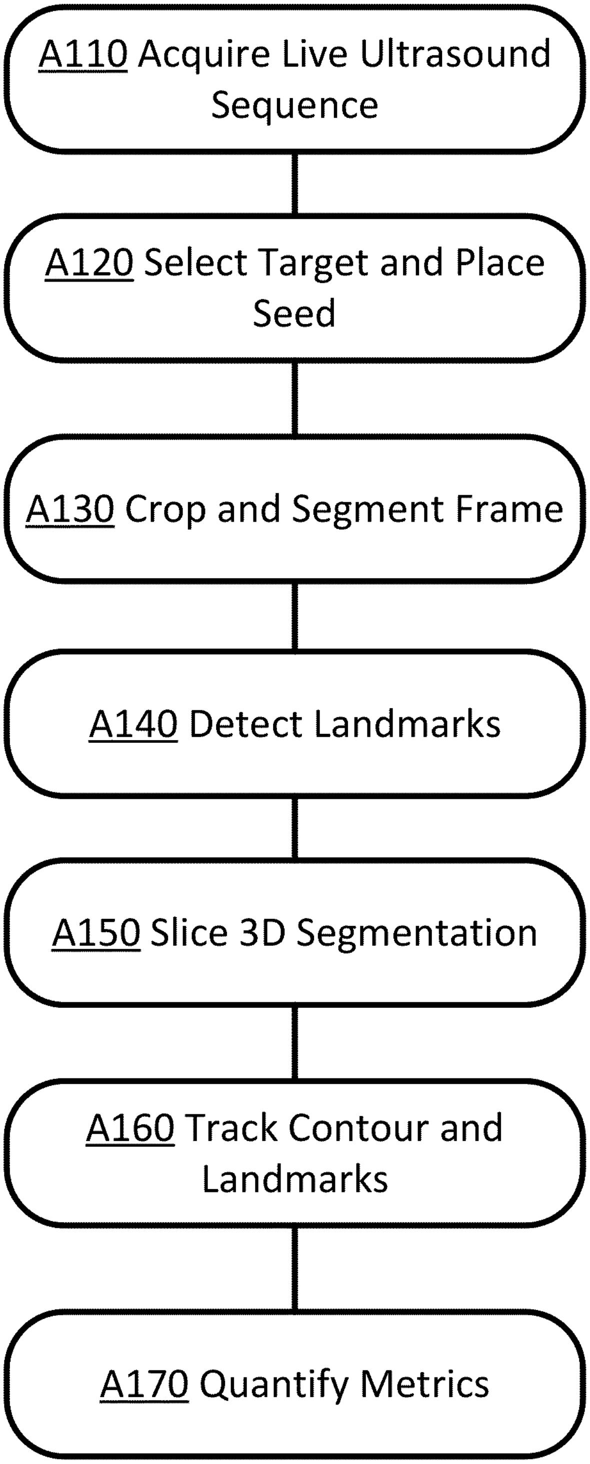
FIG. 3 depicts a flowchart for real time quantification of a 4D ultrasound sequence according to an embodiment.

FIG. 3 depicts a method for real time quantification of a 4D ultrasound sequence. Starting with a live 4D ultrasound sequence, a hybrid 3D-2D segmentation and tracking framework is used to process the high throughput data and enable real-time quantification and analysis of LAA.

At act A110, a live ultrasound sequence is acquired. The method is performed by a medical diagnostic ultrasound scanner. Plane or Volumes may be acquired. In an embodiment, the transducer of the ICE catheter provides a 3D volumetric scan. Each scan by the ICE catheter produces a 3D volume visualization of the heart. As the catheter moves (e.g., translates or rotates), different volumes are scanned. Each scan generates a frame of data representing the volume at that time. The volume of scan data may be represented by scalar values or display values (e.g., RGB) in a polar coordinate or Cartesian coordinate format. The ultrasound data may be a B-mode, color flow, or other ultrasound image. A sequence of frames of data result from the ICE imaging.

In an example, Intracardiac Echocardiography (ICE) is used to acquire images of the cardiac structures (e.g., Left atrium and Pulmonary veins). These images are used to guide the cardiologists. This requires accurate definition of the boundaries of the different anatomies. The context of use is for treatment of atrial fibrillation under the guidance of ICE imaging. The left atrium may be the most common anatomy of interest for this context.

Figure 4:
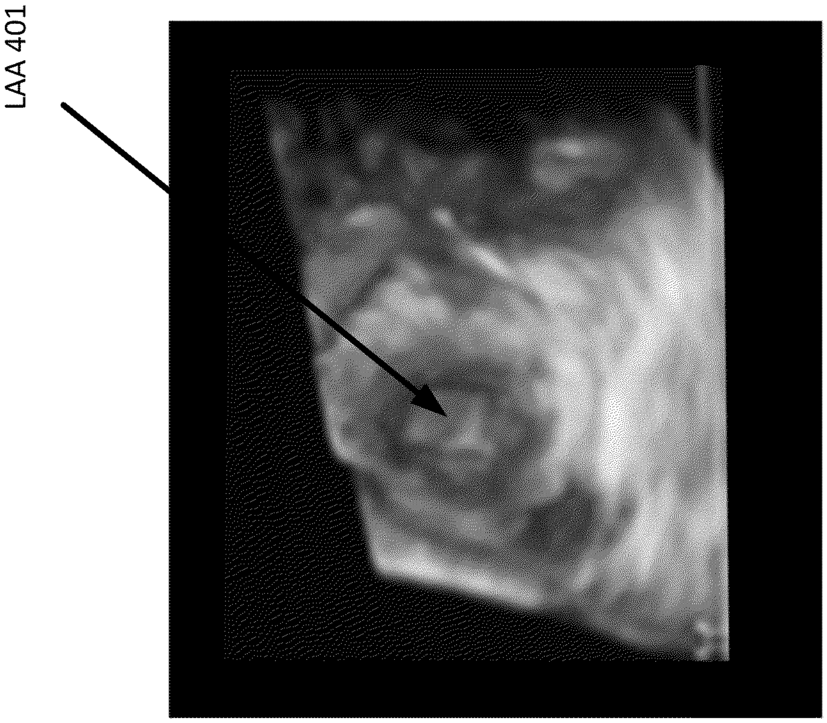
FIG. 4 depicts an example of a 3D ultrasound volume of the LAA.

The live 4D ultrasound sequence may be acquired by, for example, a 4D echo catheter, which is small enough to be inserted into the heart chambers. The 4D echo catheter allows physicians to see structures and blood flow in live motion inside the heart, which is an improvement over the standard intracardiac echo catheters that are only capable of providing 2D images. This in-motion view from inside the heart provides useful information for clinicians, especially in areas of the heart that are difficult to adequately view via transthoracic or transesophageal echo. The 4D technology provides greater visual details to guide interventional heart procedures, such as left atrial appendage closure, mitral valve repair and treatment of tricuspid valve regurgitation. Also, the 4D echo does not require the patient to be under anesthesia, which is important for patients with sedation sensitivities. FIG. 4 depicts an example of a 3D volume that includes the LAA 401. The 4D Ultrasound stream may be provided to an operator in color. A graphical interface with two or more windows may be used to depict the 3D volume and various 2D slices.

Figure 5:
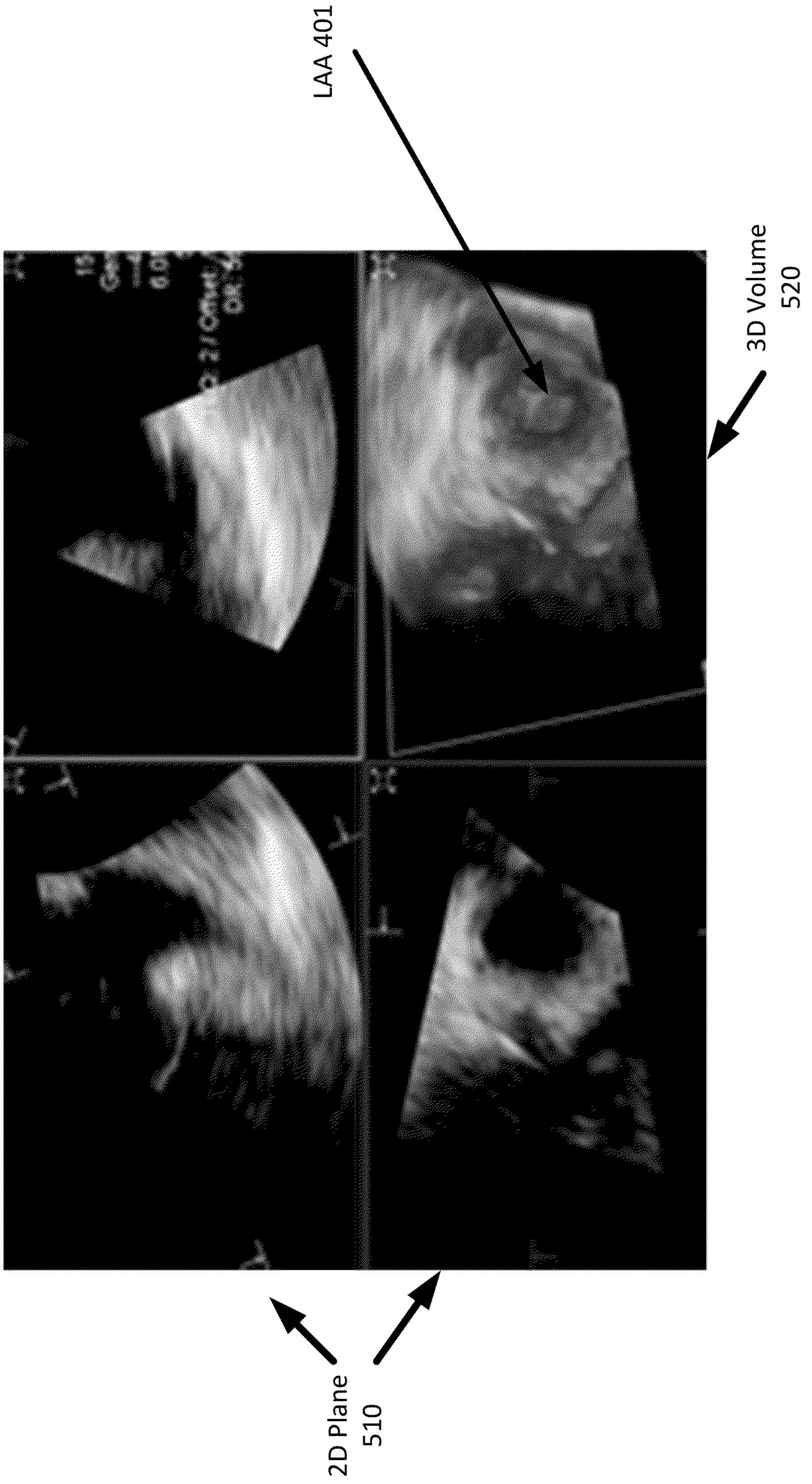
FIG. 5 depicts one view of an interface that includes 2D planes and a 3D volume of a LAA.
Figure 6:
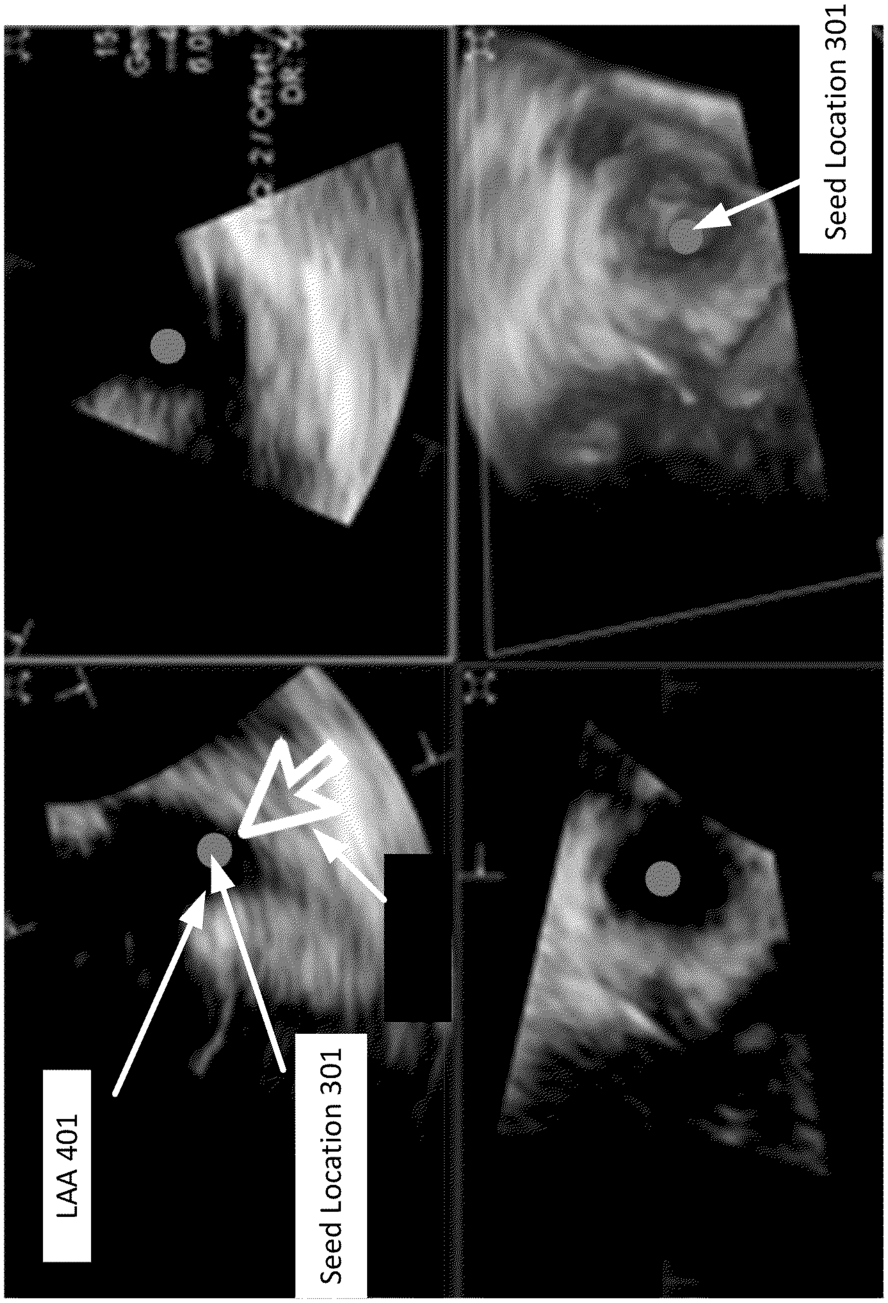
FIG. 6 depicts an example of selecting a seed location according to an embodiment.

At Act A120, a target frame is selected, and a seed is placed/located in the LAA in the selected target frame. FIG. 5 depicts a user interface that can be used to select the target frame and the seed location 301. The user interface of FIG. 5 includes a target frame that includes three images of 2D planes 510 and a representation of a 3D volume 520. The target frame include the LAA 401. The target frame may be an arbitrary frame but practically the target frame is a frame where the LAA 401 is well visualized. The frame may be selected automatically by the system or manually by an operator. FIG. 6 depicts a cursor 601 that selects or identifies the seed location 301. The seed location 301 and the depiction of the LAA 401 in this frame serve as an initial point for the temporal tracking and analysis. The seed location 301 may be placed automatically by searching the image frame for the LAA 401. Alternatively, if, for example, the frame and seed location 301 are manually selected, the user may place the seed location 301 inside LAA 401, for example, by using an input device to put a dot inside the LAA anatomy for example using the cursor 601. The seed location 301 assists the system to quickly locate a rough location of LAA 401 in the field of view and greatly reduce computational time done by searching in the whole image.

Figure 7:
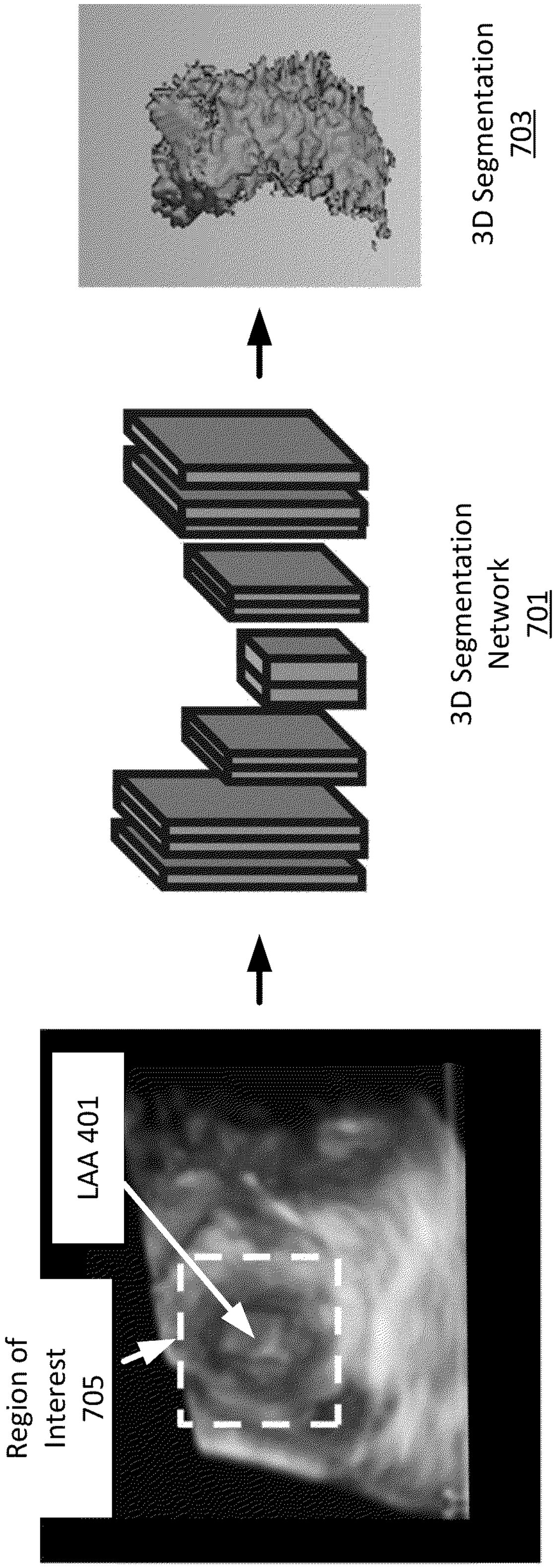
FIG. 7 depicts an example of cropping and segmenting a 3D ultrasound volume according to an embodiment.

At Act A130, the selected target frame is cropped to a region of interest 705 including the LAA 401. The LAA is then segmented by processing the region of interest 705 using a 3D segmentation network 701. FIG. 7 depicts an example of the cropping to a region of interest 705 and segmentation by a 3D segmentation network 701 that outputs a 3D segmentation 703 of the LAA 401. Different methods for cropping and segmentation may be used. The cropped region of interest 705 may be a region in which the LAA 401 (or another target organ or feature) is completely included. None of the pixels that represent the LAA 401 may be excluded. The cropped region of interest 705, however, is smaller than the target frame. By cropping the target frame to the region of interest 705, fewer computational resources may be required for the subsequent segmentation of the LAA 401 than if the entire image had to be searched/segmented. The cropped region 705 may include a buffer region around the LAA 401 so that due to movement or changes, the cropped region always includes the LAA 401.

The size of the cropped region may be determined by acquiring a dataset of potential target frames and determining a minimum size that is required to include the LAA 401.

Different methods may be used for segmentation. For example, segmentation may be thresholding-based, region-based, shape-based, model based, neighboring based, and/or machine learning-based among other segmentation techniques. Thresholding-based methods segment the image data by creating binary partitions based on image attenuation values, as determined by the relative attenuation of structures on the images. Region-based segmentation compares one pixel in an image to neighboring pixels, and if a predefined region criterion (e.g., homogeneity) is met, then the pixel/voxel is assigned to the same class as one or more of its neighbors. Shape-based techniques use either an atlas-based approach or a model-based approach to find a boundary of the LAA 401. Model-based methods use prior shape information, similar to atlas-based approaches; however, to better accommodate the shape variabilities, the model-based approaches may fit either statistical shape or appearance models of the LAA 401 to the image by using an optimization procedure. Neighboring anatomy-guided methods use the spatial context of neighboring anatomic objects. In machine learning-based methods, boundaries are predicted on the basis of the features extracted from the image data.

In at least one embodiment, a machine learned network (3D segmentation network 701) is used to crop and/or segment the LAA 401 in the region of interest. The seed location 301 may be used to guide the cropping process. A statistical prior on the shape and size of LAA 401 may be computed from a collected dataset of patients. Based on this prior, centered around the seed from previous step, the region or interest is cropped in 3D. A 3D segmentation network 701 is used to perform 3D segmentation of the LAA 401. This process may be continued in each of the following frames to generate a 4D segmentation of LAA 401. However, 3D processing with neural networks take a lot of time and thus creates challenges for real-time processing. In order to overcome this processing and temporal problem, a technical solution is applied by extracting anatomical landmarks and 2D projections of the segmentation from the 3D segmentation 703 as detailed below. The processing of 2D projections can be done in parallel and thus allow for real time 4D segmentation and analysis. This offers an efficient way of processing the high throughput data while still providing live calculation of LAA 401 statistics.

In an embodiment, the processor 110 generates a 3D segmentation 703 from input of the ICE volume to a machine-learned network 701. The 3D segmentation 703 is a labeling by voxel or location of different anatomy. The anatomy represented by each location is labeled. Alternatively, the segmentation 703 forms a 3D mesh for each anatomy. Other segmentation results may be provided. The 3D segmentation 703 provides a boundary for one or more structures in 3D. The segmentation 703 is of one or more structures of interest, such as identifying the locations of a subset or all the anatomical structures of interest for the left atrium.

The 3D segmentation 703 uses a machine-learned network 701. The ICE volume with or without other data are input to the machine-learned network 701 and a 3D segmentation 703 is output in response.

Machine learning for image segmentation may be done by extracting a selection of features from input images. These features may include, for example, pixel gray levels, pixel locations, image moments, information about a pixel's neighborhood, etc. A vector of image features is then fed into a learned classifier which classifies each pixel of the image into a class. The parameters of the classifier are learned automatically by giving the classifier input images for which the ground truth classification results is known. The output of the model can then be compared to the ground truth, and the parameters of the model are adjusted so that the model's output better matches the ground truth value. This procedure is repeated for a large amount of input images, so that the learned parameters generalize to new, unseen examples. The process of adjusting the model's parameters is referred to as training. Deep learning may also be used for segmentation, for example using a neural network. Deep learning-based image segmentation may be done, for example, using a convolutional neural network (CNN). Convolutional neural networks have a layered structure where series of convolutions are performed on an input image. Kernels of the convolutions are learned during training. The convolution results are then combined using a learned statistical model that outputs a segmented image.

The machine-learned network 701 may be an image-to-image network, such as a fully convolutional U-net trained to convert the ICE volume to the 3D segmentation. For example, the trained convolution units, weights, links, and/or other characteristics of the network are applied to the data of the ICE volume and/or derived feature values to extract the corresponding features through a plurality of layers and output the 3D segmentation. The features of the input are extracted from the ICE images as arranged in 3D. Other more abstract features may be extracted from those extracted features using the architecture. Depending on the number and/or arrangement of units or layers, other features are extracted from the input. The network includes an encoder (convolutional) network and decoder (transposed-convolutional) network forming a "U" shape with a connection between passing features at a greatest level of compression or abstractness from the encoder to the decoder. Skip connections may be provided. Any now known or later developed U-Net architectures may be used. Other fully convolutional networks may be used. In one embodiment, the network is a U-Net with one or more skip connections. The skip connections pass features from the encoder to the decoder at other levels of abstraction or resolution than the most abstract (i.e. other than the bottleneck). Skip connections provide more information to the decoding layers. A fully convolutional layer may be at the bottleneck of the network (i.e., between the encoder and decoder at a most abstract level of layers). The fully connected layer may make sure as much information as possible is encoded. Batch normalization may be added to stabilize the training.

Any machine training architecture for segmentation may be used. Similarly for other tasks described herein, different machine training architectures may be used. For example, U-Net is used. A convolutional-to-transposed-convolutional network is used. One segment of layers or units applies convolution to increase abstractness or compression. The most abstract feature values are then output to another segment. The other segment of layers or units then applies transposed convolution to decrease abstractness or compression, resulting in outputting of an indication of class membership by location. The architecture may be a fully convolutional network. Other deep networks may be used.

The network(s) used herein may be defined as a plurality of sequential feature units or layers. Sequential is used to indicate the general flow of output feature values from one layer to input to a next layer. The information from the next layer is fed to a next layer, and so on until the final output.

The layers may only feed forward or may be bi-directional, including some feedback to a previous layer. The nodes of each layer or unit may connect with all or only a sub-set of nodes of a previous or subsequent layer or unit. Within a unit or layer, any number of nodes is provided. For example, 100 nodes are provided. Later or subsequent units may have more, fewer, or the same number of nodes. The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features. Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Max pooling, upsampling, downsampling, and/or softmax layers or units may be used. Different units may be of the same or different type.

Figure 8:
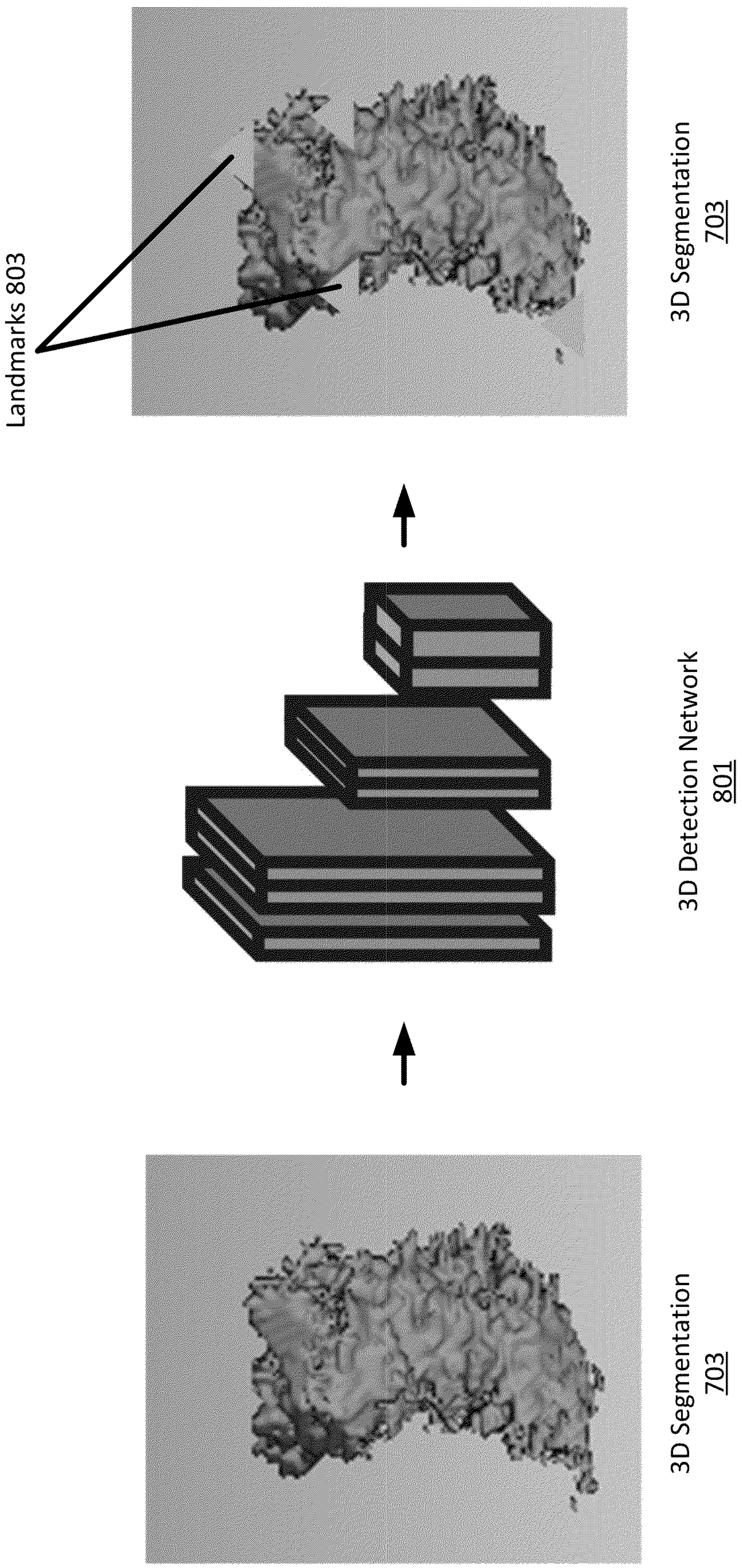
FIG. 8 depicts an example of landmark detection according to an embodiment.

At Act A140, the 3D segmentation 703 is forwarded through a 3D detection network 801 to extract important landmarks 703 for the LAA 401. This includes, for example, the ostium and neck landmarks which determines the diameters of ostium and neck area of LAA 401. FIG. 8 depicts an example of the landmark detection process including the 3D detection network 801 and a plurality of landmarks 803. Understanding the sizing of these parts is critical for determining the size of implant device. Any method for landmark detection may be used. As with the segmentation task of A130, a machine learning/deep learning method may be used. A network 801 may identify/detect landmarks based on previously annotated images/volumes. A classifier may also be used that identifies/labels voxels or pixels in the input image. The output of this act is the identification of one or more landmarks in the 3D volume/3D segmented volume.

Figure 9:
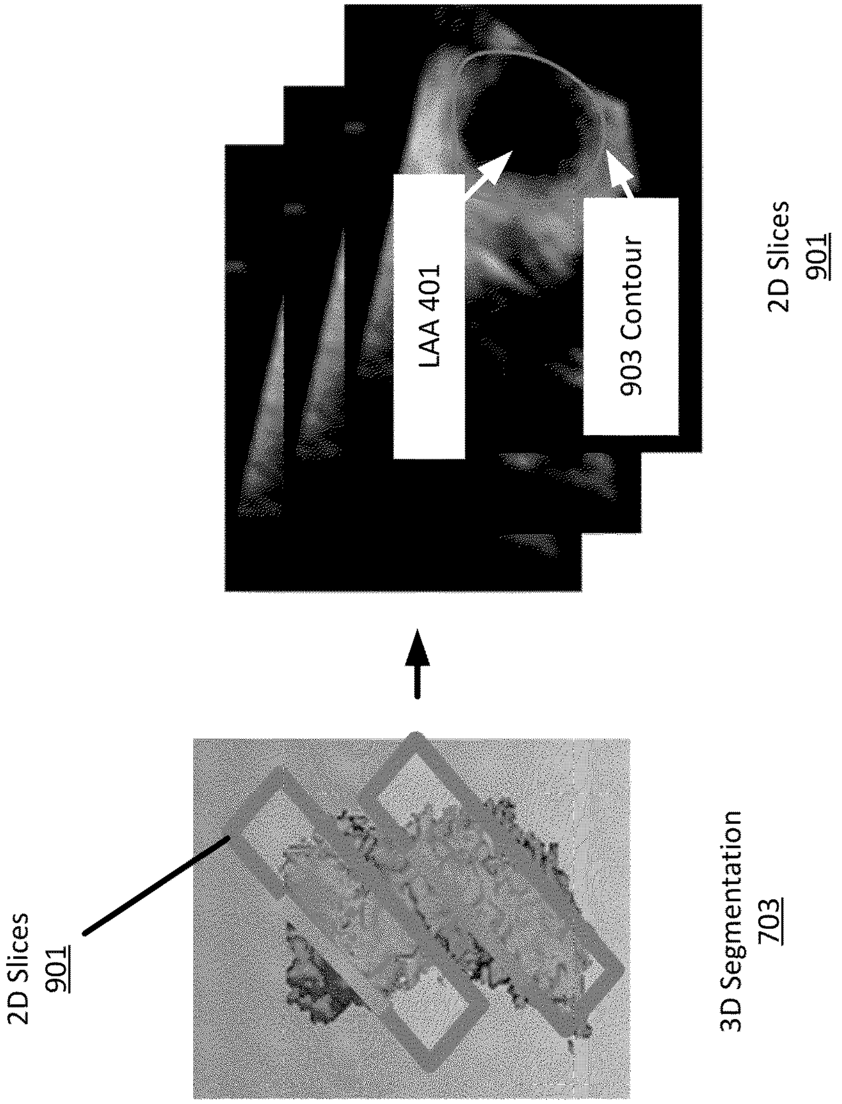
FIG. 9 depicts an example of slicing the 3D segmentation in a plurality of 2D slices according to an embodiment.

At Act A150, the 3D segmentation volume 703 of the 4D ultrasound sequence is sliced into 2D slices 901 and processed in act A160 as described below. The output of the slicing is a 2D ultrasound image with 2D contours 903 in the 2D projection of the LAA 401. For example, when the 3D segmentation 703 is sliced into 2D slices 901, each of the 2D slices 901 will contain at least some portion of the LAA segmentation 703. By slicing the 3D data into 2D slices 901, the data dimensionality is reduced to 2D which allows for parallel processing. As the slices 901 can be processed in parallel computing and contour tracking in 2D image requires less time, this improves the efficiency of the system. By slicing the data and then processing it, the systems and methods are able to provide real time tracking and analysis of the LAA 401 during a 4D ultrasound sequence. Any number of slices 901 may be used depending on the processing capabilities of the system. As depicted in FIG. 9, the 3D segmentation 703 is sliced into a plurality of 2D slices 901 that include the LAA contour 903.

At Act A160, the contour 903 and landmark(s) 803 are tracked in the 4D ultrasound sequence. From frame to frame, the contour 903 of the LAA 401 and the landmark(s) 803 are identified in the plurality of 2D slices 901, or a 3D volume generated from the 2D slices 901. Two additional neural networks may be trained to respectively track the 2D contours 903 and anatomical landmark(s) 803 accordingly. In an embodiment, a cycle-consistency loss may be used to train neural networks that perform real-time tracking of anatomical landmark(s) 803 in ultrasound images. As a contour 903 may also be discretized as a set of points, the contours 903 may also be processed using a similar network and training mechanism. In this embodiment, the 3D medical image tracking problem is treated as a motion learning process, for which the goal is to find the best motion actions based on temporary changes of neighboring frames. The motion trajectory is then tracked to locate the object of interest. Key frame features and cycle-consistency in time may also be used as two supervisory signals to learn the trajectory prediction model, which only requires a much smaller amount of annotated data compared with a supervised model. Using cycle-consistency loss is a semi-supervised learning process where only a small amount of data annotation is needed to supervise the entire training process. To improve the efficiency of the training process, a pretrained deep reinforcement learning strategy may be used where an artificial agent is trained to learn anatomical structures in static frames. The agent is able to encode the complex spatial features effectively. As the tracking problem is transformed into a motion learning problem, feature matching no longer exists. The landmarks 803 and contour 903, even with high feature ambiguity, may still be clearly located and tracked. In addition, due to the time constraints for real time analysis and quantification, the tracking networks only need to explore a small patch of neighboring area, compared with traditional methods that need to learn the whole frames. In another embodiment, a transformer-based network that uses both spatial and temporal context may be used for tracking the landmarks 903 and LAA contour 903. In an embodiment, the processed 2D slices are aggregated to generate a live 3D view that includes the contour and the landmarks.

Figure 10:
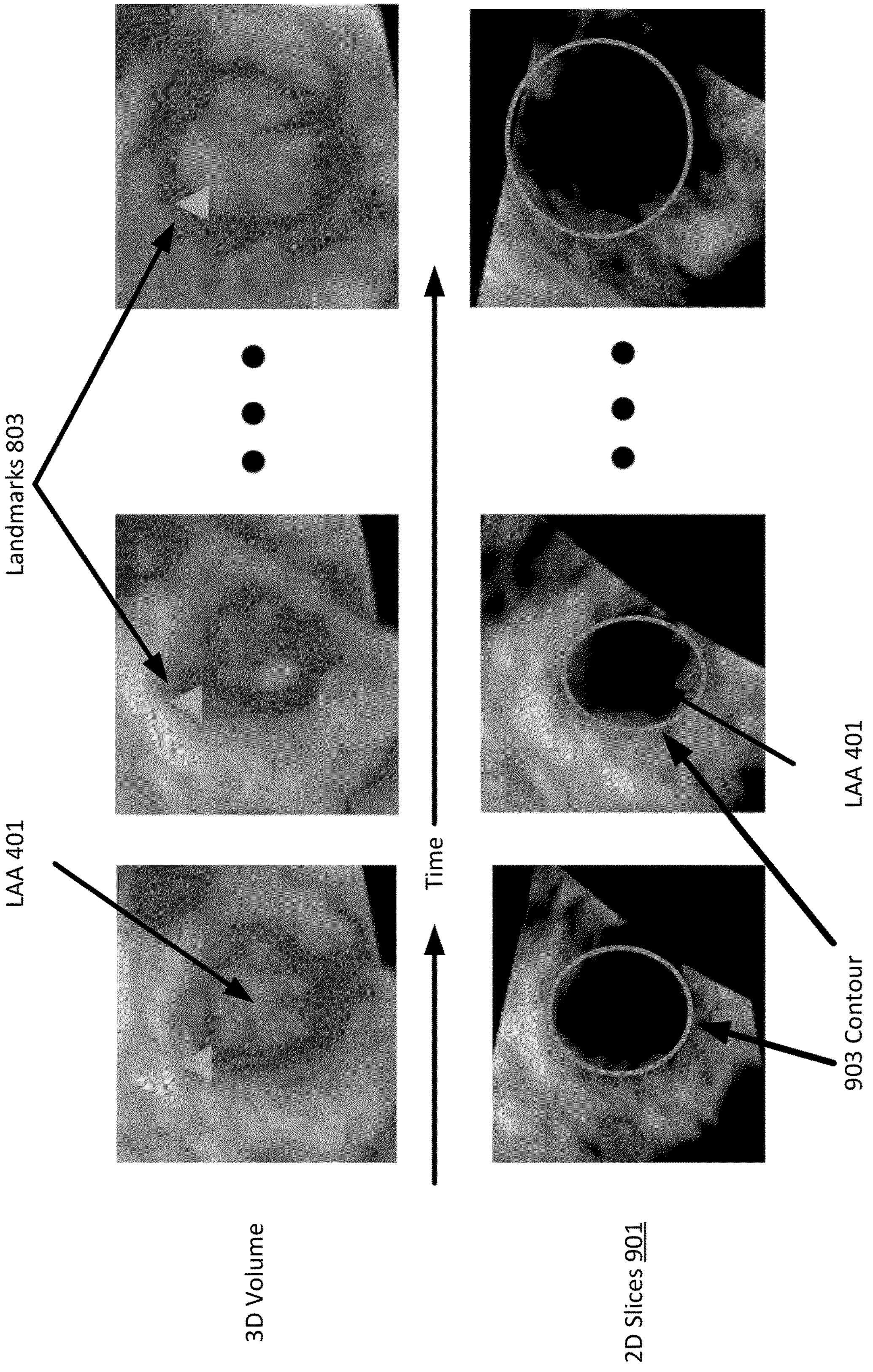
FIG. 10 depicts an example of landmark and contour tracking over time according to an embodiment.
Figure 11:
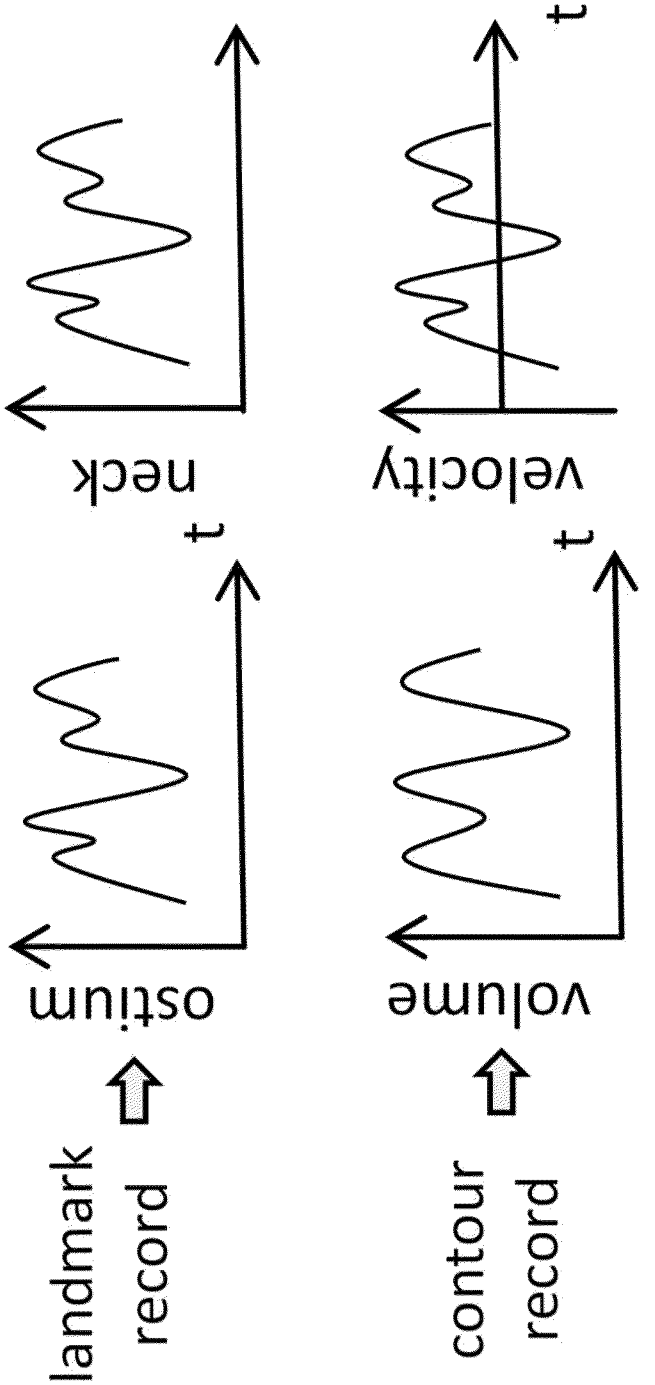
FIG. 11 depicts an example of quantifying the tracked landmarks and contour according to an embodiment.

As depicted in FIG. 10, the contour 903 is tracked frame by frame and slice by slice over time. The landmark(s) 803 may also be tracked. As depicted in FIG. 11, at Act A170, the tracked 3D landmarks 803 and 2D contours 903 are used to determine a measurement profile of the LAA 401 in real time. In one example, by tracking the ostium and the neck points on the LAA 401, the method can provide the diameter size of LAA 401 across time. This information may help determine the elasticity of LAA 401 and ultimately help choose the materials used in the device. With the tracked contours, at each frame, the 3D LAA segmentation may be reconstructed in real time with the stacking of the contours in 3D. The 3D volume and respective volume change may be identified and quantified in each frame. As there exists a positive correlation between the LAA volume and A-fib, a temporal record of LAA volume and its changes may help to better evaluate the underlying risk. Other clinically relevant metrics can also be collected with the 4D segmentation. In an example, the diameter of the LAA 401 may be used to determine and select properties of a device in a left atrial appendage closure procedure that matches characteristics of the patient's left atrial appendage.

In an embodiment, the measurement profile and other metrics may help select the device that matches the characteristics of the patient's LAA 401, leading to a patient customized care solution. Further, with the temporal aspect of the LAA measurement, the system or operator may analyze the patterns of variable changes and detects if abnormal activities exist in the LAA 401. This can help the diagnostics and early disease finding.

It is to be understood that the elements and features recited in the appended claims may be combined in different ways to produce new claims that likewise fall within the scope of the present invention. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The following is a list of non-limiting illustrative embodiments disclosed herein:

Illustrative embodiment 1. A method for real time three-dimensional left atrial appendage quantification, the method comprising: acquiring a real time three-dimensional ultrasound sequence of patient; selecting a seed location of the left atrial appendage in a frame of the real time three-dimensional ultrasound sequence; cropping the frame to a region of interest based on the seed location; generating a three-dimensional left atrial appendage segmentation from the region of interest; extracting one or more landmarks from the three-dimensional left atrial appendage segmentation; slicing the three-dimensional left atrial appendage segmentation into a plurality of two-dimensional slices, wherein the plurality of two-dimensional slices each include a portion of a contour of the left atrial appendage; tracking the contour of the left atrial appendage in the plurality of two-dimensional slices and the one or more landmarks in the real time three-dimensional ultrasound sequence; generating a real time three-dimensional left atrial appendage segmentation from the tracked contour; and quantifying at least one metric from the tracked contour and/or the tracked one or more landmarks.

Illustrative embodiment 2. The method of illustrative embodiment 1, wherein selecting the seed location comprises: freezing the real time three-dimensional ultrasound sequence; and clicking, by a user, on the seed location inside the left atrial appendage in a frame of the frozen real time three-dimensional ultrasound sequence; wherein the real time three-dimensional ultrasound sequence is unfrozen after selecting the seed location.

Illustrative embodiment 3. The method according to one of the preceding embodiments, wherein cropping comprises: calculating an estimated shape and size of the left atrial appendage from a collected dataset of images of left atrial appendages of a plurality of patients; and centering the region of interest around the seed location based on the estimated shape and size.

Illustrative embodiment 4. The method according to one of the preceding embodiments, wherein the three-dimensional left atrial appendage segmentation is generated using a machine trained network.

Illustrative embodiment 5. The method according to one of the preceding embodiments, wherein the one or more landmarks comprises at least one of ostium and neck landmarks that determine diameters of the ostium and neck area of the left atrial appendage.

Illustrative embodiment 6. The method according to one of the preceding embodiments, wherein the contour and the one or more landmarks are tracked in real time using respective neural networks trained using a cycle-consistency loss.

Illustrative embodiment 7. The method according to one of the preceding embodiments, wherein the at least one metric provides a diameter of the left atrial appendage across time.

Illustrative embodiment 8. The method of illustrative embodiment 7, wherein the diameter of the left atrial appendage is used to determine and select properties of a device in a left atrial appendage closure procedure that matches characteristics of the patient's left atrial appendage.

Illustrative embodiment 9. The method according to one of the preceding embodiments, wherein the real time three-dimensional ultrasound sequence is provided by an ultrasound system configured for Intracardiac Echocardiography.

Illustrative embodiment 10. A system for real time three-dimensional left atrial appendage segmentation, the system comprising: an ultrasound imaging system configured to acquire a 4D ultrasound sequence of patient; and a processor configured to select a seed location of the left atrial appendage in a frame of the 4D ultrasound sequence, crop the frame to a region of interest based on the seed location, generate a three-dimensional left atrial appendage segmentation from the region of interest, extract one or more landmarks from the three-dimensional left atrial appendage segmentation, slice the three-dimensional left atrial appendage segmentation into a plurality of two-dimensional slices, wherein the plurality of two-dimensional slices each include a portion of a contour of the left atrial appendage, track the contour in the plurality of two-dimensional slices over time and the one or more landmarks in the 4D ultrasound sequence, and quantify at least one metric from the tracked contour and/or the tracked one or more landmarks.

Illustrative embodiment 11. The system according to illustrative embodiment 10, wherein cropping comprises: calculating an estimated shape and size of the left atrial appendage from a collected dataset of images of left atrial appendages of a plurality of patients; and centering the region of interest around the seed location based on the estimated shape and size.

Illustrative embodiment 12. The system according to one of the preceding embodiments, wherein the processor is configured to generate the three-dimensional left atrial appendage segmentation using a machine trained network.

Illustrative embodiment 13. The system according to one of the preceding embodiments, wherein the one or more landmarks comprises at least one of ostium and neck landmarks that determine diameters of the ostium and neck area of the left atrial appendage.

Illustrative embodiment 14. The system according to one of the preceding embodiments, wherein the processor is configured to track the contour and the one or more landmarks in real time using respective neural networks trained using a cycle-consistency loss.

Illustrative embodiment 15. The system according to one of the preceding embodiments, wherein the at least one metric provides a diameter of the left atrial appendage across time.

Illustrative embodiment 16. The system according to illustrative embodiment 15, wherein the diameter of the left atrial appendage is used to determine and select properties of a device in a left atrial appendage closure procedure that matches characteristics of the patient's left atrial appendage.

Illustrative embodiment 17. The system according to one of the preceding embodiments, wherein the ultrasound imaging system is configured for Intracardiac Echocardiography.

Illustrative embodiment 18. A system comprising: an ultrasound imaging system configured to acquire a 4D ultrasound sequence of patient; a display configured to display the 4D ultrasound sequence; an input device configured to identify a seed location for a left atrial appendage in a frame of the 4D ultrasound sequence; and a processor configured to crop the frame to a region of interest based on the seed location, generate a three-dimensional left atrial appendage segmentation from the region of interest, slice the three-dimensional left atrial appendage segmentation into a plurality of two-dimensional slices, wherein the plurality of two-dimensional slices each include a portion of a contour of the left atrial appendage, track the contour in the plurality of two-dimensional slices in real time, and generate a real time three-dimensional left atrial appendage segmentation from the tracked contour.

Illustrative embodiment 19. The system according to one of the preceding embodiments, wherein the processor is further configured to identify one or more landmarks in the three-dimensional left atrial appendage segmentation and track the one or more landmarks over time in the 4D ultrasound sequence.

Illustrative embodiment 20. The system according to one of the preceding embodiments, wherein the processor is further configured to quantify at least one metric from the real time three-dimensional left atrial appendage segmentation and/or the tracked one or more landmarks.

The invention claimed is:

1. A method for real time three-dimensional left atrial appendage quantification, the method comprising:

acquiring a real time three-dimensional ultrasound sequence of a patient;

selecting a seed location of the left atrial appendage in a frame of the real time three-dimensional ultrasound sequence;

cropping the frame to a region of interest based on the seed location;

generating an initial three-dimensional left atrial appendage segmentation from the region of interest;

extracting one or more landmarks from the three-dimensional left atrial appendage segmentation;

slicing the initial three-dimensional left atrial appendage segmentation into a plurality of two-dimensional slices, wherein the plurality of two-dimensional slices each include a portion of a contour of the left atrial appendage;

tracking the contour of the left atrial appendage in the plurality of two-dimensional slices for a plurality of subsequent frames of the real time three-dimensional ultrasound sequence and tracking the one or more landmarks in the real time three-dimensional ultrasound sequence;

generating a real time three-dimensional left atrial appendage segmentation for each of the plurality of subsequent frames by aggregating the tracked contours from the two-dimensional slices for each respective subsequent frame; and quantifying at least one morphological metric from the tracked contour and/or the tracked one or more landmarks, wherein the at least one morphological metric comprises a diameter of the left atrial appendage over time, wherein the quantified diameter is used to determine a property of a device in a left atrial appendage closure procedure.

2. The method of claim 1, wherein selecting the seed location comprises:

freezing the real time three-dimensional ultrasound sequence; and clicking, by a user, on the seed location inside the left atrial appendage in a frame of the frozen real time three-dimensional ultrasound sequence;

wherein the real time three-dimensional ultrasound sequence is unfrozen after selecting the seed location.

3. The method of claim 1, wherein cropping comprises:

calculating an estimated shape and size of the left atrial appendage from a collected dataset of images of left atrial appendages of a plurality of patients; and centering the region of interest around the seed location based on the estimated shape and size.

4. The method of claim 1, wherein the three-dimensional left atrial appendage segmentation is generated using a machine trained network.

5. The method of claim 1, wherein the one or more landmarks comprises at least one of ostium and neck landmarks that determine diameters of the ostium and neck area of the left atrial appendage.

6. The method of claim 1, wherein the contour and the one or more landmarks are tracked in real time using respective neural networks trained using a cycle-consistency loss.

7. The method of claim 1, wherein the diameter of the left atrial appendage is used to determine and select properties of the device in the left atrial appendage closure procedure that matches characteristics of the patient's left atrial appendage.

8. The method of claim 1, wherein the real time three-dimensional ultrasound sequence is provided by an ultrasound system configured for Intracardiac Echocardiography.

9. A system for real time three-dimensional left atrial appendage segmentation, the system comprising:

an ultrasound imaging system configured to acquire a 4D ultrasound sequence of patient; and a processor configured to:

select a seed location of the left atrial appendage in a frame of the 4D ultrasound sequence, crop the frame to a region of interest based on the seed location, generate an initial three-dimensional left atrial appendage segmentation from the region of interest, extract one or more landmarks from the initial three-dimensional left atrial appendage segmentation, slice the initial three-dimensional left atrial appendage segmentation into a plurality of two-dimensional slices, wherein the plurality of two-dimensional slices each include a portion of a contour of the left atrial appendage, track the contour in the plurality of two-dimensional slices over time and the one or more landmarks in the 4D ultrasound sequence, generate a real time three-dimensional left atrial appendage segmentation for each of the plurality of subsequent frames by aggregating the tracked contours from the two-dimensional slices for each respective subsequent frame, quantify at least one morphological metric from the tracked contour and/or the tracked one or more landmarks, wherein the at least one morphological metric comprises a diameter of the left atrial appendage over time, and cause a display to present the quantified diameter for use in determining a property of a device in a left atrial appendage closure procedure.

10. The system of claim 9, wherein cropping comprises:

calculating an estimated shape and size of the left atrial appendage from a collected dataset of images of left atrial appendages of a plurality of patients; and centering the region of interest around the seed location based on the estimated shape and size.

11. The system of claim 9, wherein the processor is configured to generate the three-dimensional left atrial appendage segmentation using a machine trained network.

12. The system of claim 9, wherein the one or more landmarks comprises at least one of ostium and neck landmarks that determine diameters of the ostium and neck area of the left atrial appendage.

13. The system of claim 9, wherein the processor is configured to track the contour and the one or more landmarks in real time using respective neural networks trained using a cycle-consistency loss.

14. The system of claim 9, wherein the diameter of the left atrial appendage is used to determine and select properties of the device in the left atrial appendage closure procedure that matches characteristics of the patient's left atrial appendage.

15. The system of claim 9, wherein the ultrasound imaging system is configured for Intracardiac Echocardiography.

16. A system comprising:

an ultrasound imaging system configured to acquire a 4D ultrasound sequence of patient;

a display configured to display the 4D ultrasound sequence;

an input device configured to identify a seed location for a left atrial appendage in a frame of the 4D ultrasound sequence; and a processor configured to:

crop the frame to a region of interest based on the seed location, generate an initial three-dimensional left atrial appendage segmentation from the region of interest, slice the initial three-dimensional left atrial appendage segmentation into a plurality of two-dimensional slices, wherein the plurality of two-dimensional slices each include a portion of a contour of the left atrial appendage, track the contour in the plurality of two-dimensional slices in real time, generate a real time three-dimensional left atrial appendage segmentation for each of the plurality of subsequent frames by aggregating the tracked contours from the two-dimensional slices for each respective subsequent frame, identify one or more landmarks in the three-dimensional left atrial appendage segmentation and track the one or more landmarks over time in the 4D ultrasound sequence, and quantify at least one metric from the real time three-dimensional left atrial appendage segmentation and/or the tracked one or more landmarks.

* * * * *